United States Patent [19]

Morrison et al.

[11] Patent Number: 5,869,074
[45] Date of Patent: Feb. 9, 1999

[54] PESTICIDAL COMPOSITIONS

[75] Inventors: Bruce Jon Morrison; Dean Bruce Morrison; Adam Morrison, all of Helensvale, Australia

[73] Assignee: MJA Scientifics International Pty. Ltd., Southport, Australia

[21] Appl. No.: 868,492

[22] Filed: Apr. 15, 1992

Related U.S. Application Data

[63] Continuation-in-part of Ser. No. 617,030, Nov. 21, 1990, abandoned.

[30] Foreign Application Priority Data

Nov. 23, 1989 [AU] Australia ................................ PJ7527

[51] Int. Cl.$^6$ ................... A01N 25/10; A01N 57/12; A01N 57/16
[52] U.S. Cl. ................... 424/410; 424/405; 514/772.3
[58] Field of Search ..................... 424/405, 400, 424/410, 484, 486, 84; 43/132.1; 219/678; 514/772.3, 89; 558/116

[56] References Cited

U.S. PATENT DOCUMENTS

| 2,956,073 | 11/1960 | Whetstone et al. | 558/116 |
|---|---|---|---|
| 3,244,586 | 4/1966 | Rigterink | 514/89 |
| 4,049,460 | 9/1977 | Broadbent | 424/84 |
| 4,102,991 | 7/1978 | Uydonieus | 424/27 |
| 4,160,824 | 7/1979 | Inazuka et al. | 424/84 |
| 4,205,066 | 5/1980 | Hennart et al. | 424/84 |
| 4,303,642 | 12/1981 | Kangas | 514/89 |
| 4,514,960 | 5/1985 | Sears | 424/84 |
| 4,554,155 | 11/1985 | Allan et al. | 424/419 |
| 4,639,393 | 1/1987 | Von Kohorn et al. | 428/309.4 |
| 4,670,250 | 6/1987 | Baker | 424/84 X |
| 4,707,355 | 11/1987 | Wilson | 424/410 X |
| 4,990,514 | 2/1991 | Braey | 514/275 |
| 5,690,951 | 11/1997 | Lew et al. | 424/410 |

*Primary Examiner*—Robert H. Harrison
*Attorney, Agent, or Firm*—Larson & Taylor

[57] ABSTRACT

The pesticidal composition of the invention comprises dichlorvos and chlorpyrifos. The composition is prepared by combining the components together and then subjecting the mixture to microwave radiation. The resultant composition exhibits a synergistic effect on the individual properties of the respective components which not only quickly exterminates existing pests but which also leaves a residual pesticidal protection which is not readily removed by conventional cleaning processes. The composition is particularly effective against cockroaches.

9 Claims, No Drawings

PESTICIDAL COMPOSITIONS

CROSS-REFERENCE TO RELATED APPLICATIONS

This application is a continuation-in-part of U.S. application Ser. No. 07/617,030 filed Nov. 21, 1990, now abandoned.

FIELD OF THE INVENTION

THIS INVENTION relates to pesticidal compositions. In particular, it is directed to compositions containing both fumigant and residual pesticidal ingredients which function first to exterminate quickly any pests immediately present but then leave a residual protection against pests in the area or on the surfaces to which the composition has been applied.

BACKGROUND OF THE INVENTION

There are many domestic and commercial applications wherein areas and surfaces must be protected against infestation by insects and other pests. For example, household cupboards, wardrobes, pantries and the like must be protected against invasion by ants, cockroaches and other pests. Similarly, in commercial premises and establishments such as restaurants, cafes and the like it is essential, and often mandatory under government health regulations, that areas used for the storage of food and/or the preparation and serving of meals be kept pest free.

Of particular concern are German cockroaches. These pests have a marked resistance to most of the known pesticides, including the synthetic pyrethroids. Conventional treatments only remove this species of cockroach for a period between several days and three months. Further, conventional treatments do not affect any eggs which may have been deposited by the female cockroach. Accordingly, the eggs hatch and re-infestation occurs.

In the past, organo phosphates were the preferred choice for the extermination and control of these pests, although they have been virtually superceded today by synthetic pyrethroids and carbamates. However, two well-known organo phosphates still in use are dichlorvos and chlorpyrifos. Dichlorvos is commonly used as a fumigant and thus used when it is necessary to kill pests already present in an affected area. Chlorpyrifos is a residual and is, therefore, utilised to keep an already cleared area free from pests. It is primarily used as a surface spray for short to medium-term residual control. Commercial suppliers of chlorpyrifos estimate its effective life to be approximately three (3) months. Nevertheless, individually, neither dichlorvos nor chlorpyrifos are considered to be very effective.

It is also known to provide a pesticidal composition which is a combination of fumigant and residual ingredients. In fact, dichlorvos has been used as an additive to a residual-type pesticide. Although when used as such an additive, dichlorvos does reduce the "knockdown" time required to eliminate existing pests, it does not increase the effective life of the residual ingredient to which it has been added. For this reason, dichlorvos is rarely used now in the pest control industry as the extra expense incurred in its inclusion in the composition to reduce the immediate numbers of pests present is not outweighed by any lasting advantage of the residual component.

Further, a disadvantage of the residual chlorpyrifos is that it is readily removed by cleaning of treated surfaces, such cleaning, of course, being a regular occurrence in food storage, preparation and serving areas.

Yet another disadvantage of prior pesticidal compositions, whether they contain residual ingredients or not, is that a pest usually must remain in a treated area for a sufficient period for the pesticidal composition to be effective. If the pest remains for that sufficient period, then often enough contact with the active ingredient has been made to eradicate the pest, even if the pest first leaves the treated area before dying. On the other hand, if the pest leaves the treated area before sufficient contact is made with the active ingredient, then the pest may again return to the area as it is unaware that that environment is hostile to it.

SUMMARY OF THE INVENTION

It is a general object of the present invention to overcome, or at least ameliorate, one or more of the above problems and to provide a pesticidal composition containing both fumigant and residual ingredients which not only quickly exterminates existing pests but which also leaves a residual pesticidal protection which is not readily removed by conventional cleaning processes.

The present inventors have discovered that the general object can be achieved by first mixing dichlorvos and chlorpyrifos together and then subjecting the mixture to microwave radiation.

Thus according to a first aspect of the present invention, there is provided a pesticidal composition, said composition comprising dichlorvos and chlorpyrifos which have been added together and then subjected to microwave radiation.

In addition to the active ingredients, the compositions of the present invention may optionally include other, non-active ingredients, such as the usual diluents and carriers.

For example, the life of the composition can be further extended by the addition of a high molecular weight polymer to adjust the viscosity of the composition.

Another optional feature of the compositions of the present invention is the addition of a pest attractant, for example, a sweetening agent.

According to a second aspect of the present invention, there is provided a process for the preparation of a pesticidal composition, said processing comprising:

1) mixing together dichlorvos and chlorpyrifos; and
2) subjecting the thus obtained mixture to microwave radiation;

whereupon the resultant composition may have added, optionally, any required diluent, carrier or other ingredient.

Preferably, the composition also includes a high molecular weight polymer. More preferably, this high molecular weight polymer is polyvinyl alcohol (PVA).

Optionally, the composition may include sugar as a sweetening agent to attract pests to the treated area.

DESCRIPTION OF THE INVENTION

Examples of the compositions of the present invention and methods for their preparation will now be described.

In these examples, a reference to chlorpyrifos concentrate is a reference to the commercially available concentrate of chlorpyrifos (450 gm/l) in xylene (300 gm/l), with the balance being emulsifiers and/or other non-active components; a reference to dichlorvos concentrate is a reference to the commercially available concentrate of dichlorvos (505 gm/l) in xylene (455 gm/l), with the balance being emulsifiers and/or other non-active components; and a reference to microwave radiation is a reference to microwave irradiation of 12 cms wavelength at 600 watts for 20 seconds.

EXAMPLE 1

Commercially available dichlorvos (150 ml) and chlorpyrifos (150 ml) concentrates are mixed together and then subjected to microwave radiation. The mixture is diluted with 9 litres of water.

EXAMPLE 2

Commercially available dichlorvos (100 ml) and chlorpyrifos (100 ml) concentrates are mixed together and then subjected to microwave radiation. The mixture is diluted with 9 litres of water.

EXAMPLE 3

Polyvinyl alcohol (100 ml) was added to the composition of Example 1.

EXAMPLE 4

Commercially available dichlorvos (120 ml) and chlorpyrifos (180 ml) concentrates are mixed together, subjected to microwave radiation and added slowly to polyvinyl alcohol (200 ml) in water (2 L) with agitation and then further diluted with water (8 L). Sugar (400 g) dissolved in hot water is added as a sweetening agent which attracts pests to the area to be treated.

To establish the benefit of subjecting the mixtures of dichlorvos and chlorpyrifos to microwave radiation, a further composition was prepared whereby commercially available dichlorvos (150 ml) and chlorpyrifos (150 ml) concentrates were simply mixed together and added to 9 litres of water. The results of using this composition on commercial and residential properties are presented in Table 1.

The results of using the compositions of the present invention as described in Examples 1 and 2 above are presented in Tables 2 and 3 respectively.

TABLE 1

PESTICIDAL COMPOSITION - 150 mls Dichlorvos + 150 mls Chlorpyrifos mixed and agitated then added to 9 liters of water.

| PROPERTY ADDRESS | DATE OF JOB | TIME OF JOB | DESCRIPTION OF INFESTATION | INITIAL K.O. | INITIAL KILL | PERFORMANCE | | | | | |
|---|---|---|---|---|---|---|---|---|---|---|---|
| | | | | | | 3 mths | 6 mths | 9 mths | 12 mths | 15 mths | 18 mths |
| La Rustica Restaurant Surfers Paradise | 19/06/89 | 11:30 pm | Heavy Infestation of German Cockroaches | 10–20 secs | 100% | No Activity | No Activity | Minor Activity | Renewed Contract | | |
| Belisimo Restaurant Broadbeach | 20/06/89 | 11:00 pm | Moderate Infestation of German & Oriental Cockroaches | 10–20 secs | 100% | No Activity | Minor Activity Serviced | No Activity | No Activity | Renewed Contract | |
| Ocean View Motel Coolangatta | 23/06/89 | 9:30 am | German Cockroaches - Moderate Infestation in rooms Heavy Infestation in Restaurant | 10–20 secs | 100% | No Activity | Minor Activity Serviced | No Activity | Minor Activity | Renewed Contract | |
| Tunnel Nightclub Surfers Paradise | 26/06/89 | 10:00 am | Moderate Infestation - German, American, Australian Cockroaches | 10–20 secs | 100% | Minor Activity Serviced | No Activity | Minor Activity Serviced | Renewed Contract | | |
| Sam-The-Wok Restaurant Chevron Island | 27/06/89 | 9:00 am | Moderate Infestation of German Cockroaches | 10–20 secs | 100% | No Activity | No Activity | No Activity | Renewed Contract | | |
| Tandoori Taj Restaurant Surfers Paradise | 01/07/89 | 11:30 pm | Heavy Infestation - German, American, Oriental Cockroaches | 10–20 secs | 100% | No Activity | No Activity | Minor Activity Serviced | Renewed Contract | | |
| Chevron Island Coffee Shop | 05/07/89 | 6:00 am | Heavy Infestation of German Cockroaches | 10 secs | 100% | Minor Activity Serviced | No Activity | No Activity | No Activity | Renewed Contract | |
| The Avenue Restaurant & Bar Surfers Paradise | 14/07/89 | 6:00 am | Moderate Infestation - German American, Australian | 10–20 secs | 100% | No Activity | Minor Activity Serviced | No Activity | Renewed Contract | | |
| Frog Hollow House Boat Sanctuary Cove | 15/07/89 | 11:00 am | Heavy Infestation of German Cockroaches | 10 secs | 100% | No Activity | No Activity | Minor Activity | Renewed Contract | | |

TABLE 2

PESTICIDAL COMPOSITION - 150 mls Dichlorvos + 150 mls Chlorpyrifos mixed, agitated and microwaved then added to 9 liters of water.

| PROPERTY ADDRESS | DATE OF JOB | TIME OF JOB | DESCRIPTION OF INFESTATION | INITIAL K.O. | INITIAL KILL | PERFORMANCE | | | | | |
|---|---|---|---|---|---|---|---|---|---|---|---|
| | | | | | | 3 mths | 6 mths | 9 mths | 12 mths | 15 mths | 18 mths |
| Stage Door Theatre Restaurant Chevron Island | 20/06/89 | 12:30 pm | Heavily Infested with German & Australian Cockroaches | 5–10 secs | 100% | No Activity | No Activity | No Activity | No Activity | No Activity | No Activity |
| Grapevine Restaurant Southport | 25/06/89 | 10:00 am | Very Heavy Infestation of German Cockroaches | 5–10 secs | 100% | No Activity | No Activity | No Activity | No Activity | No Activity | No Activity |
| Charlies Restaurant Surfers Paradise | 26/06/89 | 6:00 am | Moderate Infestation of German Cockroaches | 5–10 secs | 100% | No Activity | No Activity | No Activity | Renewed Contract | | |
| Fawity Tacos Restaurant Main Beach | 17/07/89 | 10:30 am | Moderate Infestation of German & American Cockroaches | 5–10 secs | 100% | No Activity | No Activity | No Activity | No Activity | No Activity | Renewed Contract |
| Mexican Kitchen Restaurant Bundall | 17/07/89 | 11:30 pm | German Cockroaches - Heavy Infestation in dishwasher. | 5–10 secs | 100% | No Activity | No Activity | No Activity | Renewed Contract | | |
| Copper Pan Restaurant Broadbeach | 19/07/89 | 7:00 am | Moderate Infestation of German, American & Oriental Cockroaches. | 5–15 secs | 100% | No Activity | No Activity | No Activity | No Activity | Renewed Contract | |
| Residential Property Thornton Street, Surfers Paradise | 19/07/89 | 9:30 am | Heavy Infestation of German & American Cockroaches. | 5–10 secs | 100% | No Activity | No Activity | No Activity | No Activity | No Activity | No Activity |
| Pellermans Hotel Nerang | 24/07/89 | 10:15 pm | Heavy Infestation - German, Australian, Oriental & American. | 5–20 secs | 100% | No Activity | No Activity | No Activity | Renewed Contract | | |
| Cornelius Cruise Vessel Mariners Cove | 19/08/89 | 8:30 am | Very Heavy Infestation - All Species. | 5–20 secs | 100% | No Activity | No Activity | No Activity | No Activity | No Activity | No Activity |

TABLE 3

PESTICIDAL COMPOSITION - 100 mls Dichlorvos + 100 mls Chlorpyrifos mixed, agitated and microwaved then added to 9 liters of water.

| PROPERTY ADDRESS | DATE OF JOB | TIME OF JOB | DESCRIPTION OF INFESTATION | INITIAL K.O. | INITIAL KILL | PERFORMANCE | | | | | |
|---|---|---|---|---|---|---|---|---|---|---|---|
| | | | | | | 3 mths | 6 mths | 9 mths | 12 mths | 15 mths | 18 mths |
| Sweethearts Cafe Surfers Paradise | 01/09/89 | 7:00 pm | Heavy Infestation of German Cockroaches | 10–15 secs | 100% | No Activity | No Activity | No Activity | Renewed Contract | | |
| Als Coffee Lounge Southport | 02/09/89 | 3:00 pm | Heavy Infestation of German & American Cockroaches | 10–15 secs | 100% | No Activity | No Activity | Minor Activity | Renewed Contract | | |
| Commercial Hotel Nerang | 05/09/89 | 7:00 am | Moderate Infestation - All Species | 10–15 secs | 100% | No Activity | No Activity | No Activity | Renewed Contract | | |
| Draculas Theatre Restaurant Broadbeach | 16/09/89 | 9:00 am | Heavy Infestation - All Species | 10–15 Secs | 100% | No Activity | No Activity | Minor Activity | Renewed Contract | | |
| City Fisheries Ashmore | 18/09/89 | 7:20 am | Heavy Infestation of German Cockroaches. | 10–15 secs | 100% | No Activity | No Activity | No Activity | No Activity | Renewed Contract | |
| Runaway Bay Poultry Runaway Bay | 27/09/89 | 9:00 pm | Heavy Infestation of German Cockroaches. | 10–15 secs | 100% | No Activity | No Activity | No Activity | Renewed Contract | | |
| Coolangatta Senior Citizens Club Coolangatta | 06/10/89 | 4:00 pm | Very Heavy Infestation - All Species | 10–15 secs | 100% | No Activity | No Activity | No Activity | No Activity | Renewed Contract | |
| Residential Property Amalfi Street Isle of Capri | 10/10/89 | 11:00 am | Moderate Infestation of German & American Cockroaches. | 10–15 secs | 100% | Minor Activity | No Activity | No Activity | No Activity | No Activity | Renewed Contract |
| Residential Property River Road | 14/10/89 | 10:00 am | Moderate Infestation of German & | 10–15 secs | 100% | No Activity | Minor Activity | No Activity | No Activity | Renewed Contract | |

TABLE 3-continued

PESTICIDAL COMPOSITION - 100 mls Dichlorvos + 100 mls Chlorpyrifos mixed, agitated and microwaved then added to 9 liters of water.

| PROPERTY ADDRESS | DATE OF JOB | TIME OF JOB | DESCRIPTION OF INFESTATION | INI- TIAL K.O. | INI- TIAL KILL | PERFORMANCE | | | | | |
|---|---|---|---|---|---|---|---|---|---|---|---|
| | | | | | | 3 mths | 6 mths | 9 mths | 12 mths | 15 mths | 18 mths |
| Cypress Gardens | | | American Cockroaches. | | | | | | | | |

Clearly, the quantity required of the compositions of the present invention will vary dependent on the size of the area to be heated. However, as a general illustration of quantities required, the 9 litres of Example 1 will treat 200 sq.m.

From the results presented in Tables 1 to 3, the following should be noted:

(a) The compositions of the present invention are clearly superior to the comparative example. Re-infestation of the treated area occurs within 3 to 6 months using the comparative example, in contrast to the present invention wherein there is no sign of re-infestation at 9, 12, 15 or 18 months.

In fact, it is anticipated that the compositions of the present invention will remain effective past 18 months—the results presented in Tables 2 and 3 were truncated simply because re-treatment was undertaken to ensure that re-infestation would not occur again, even though there was no indication that the effectiveness of the current treatment had lapsed.

(b) The average effectiveness of the comparative example is 7 months, whereas it is 16 months for Example 1 of the present invention and 10 months for Example 2 of the present invention.

(c) The results obtained from Example 2 of the present invention, when compared to the comparative example, establish that microwave irradiation of a mixture of dichlorvos and chlorpyrifos enables a 30% reduction in active ingredients to provide a 40% increase in effective life of the treatment.

It should also be noted that the alcoholic composition of Example 3 can be conveniently applied to light covers whereupon the heat emitted by lights when in operation releases the dichlorvos thus killing mosquitoes and other flying insects which are attracted to the lights.

Major advantages of the present invention thus include (1) the compositions exhibit a synergistic effect on the properties of the respective components either individually or as a mixture; (2) significantly less quantities of individual ingredients are required to achieve this synergistic effect; and (3), although not wishing to be bound by theory, the presence of the composition in the treated area appears to prevent female pests from depositing eggs thereon, thus significantly reducing the likelihood of re-infestation.

A further advantage is that the compositions provide a positive repelling effect. Due to the efficacious residual action of the present invention, pests such as cockroaches which take in air from underneath their bodies and thus have their lungs in close proximity to the treated surface, become immediately aware that the environment is hostile resulting in a retreat by the pest.

By using the compositions of the present invention, effective and continual protection against insects such as cockroaches, mosquitoes, ants and midges can be achieved, although it will be appreciated that the above examples are given by way of exemplification of the invention only, and that changes may be made to the details set out therein without departing from the scope of the invention as defined in the following claims.

We claim:

1. A method of extending the life of a pesticidal composition comprising a mixture of dichlorvos and chlorpyrifos, said method comprising subjecting said mixture to microwave radiation to extend the life of the pesticidal composition.

2. The method defined in claim 1 further comprising the step of adding a polymer to said mixture after said mixture is subjected to microwave radiation to adjust viscosity of said mixture.

3. The method defined in claim 2, wherein said polymer comprises polyvinyl alcohol.

4. The method defined in claim 1 further comprising the step of adding a sweetening agent to said mixture after said mixture is subjected to microwave radiation.

5. The method defined in claim 4 wherein said sweetening agent comprises sugar.

6. The method defined in claim 1 wherein said mixture of dichlorvos and chlorpyrifos comprises approximately 1 part of each dichlorvos and chlorpyrifos per 60 parts water.

7. The method defined in claim 1 wherein said mixture of dichlorvos and chlorpyrifos comprises approximately 1 part of each dichlorvos and chlorpyrifos per 90 parts water.

8. A pesticidal composition having improved residual pesticidal protection prepared by the method of claim 1.

9. A pesticidal composition having improved residual pesticidal protection prepared by the method of claim 2.

* * * * *

UNITED STATES PATENT AND TRADEMARK OFFICE
CERTIFICATE OF CORRECTION

PATENT NO.   : 5,869,074
DATED        : February 9, 1999
INVENTOR(S)  : MORRISON et al.

It is certified that error appears in the above-indentified patent and that said Letters Patent is hereby corrected as shown below:

On the title page, item:
 [73] Assignee:   FLAMESTAR Pty. Ltd.
                  Southport, Queensland, AUSTRALIA Signed and Sealed this Twenty-eighth Day of December, 1999

Attest:

Q. TODD DICKINSON

Attesting Officer

Acting Commissioner of Patents and Trademarks